(12) United States Patent
Duesbury et al.

(10) Patent No.: US 7,772,578 B2
(45) Date of Patent: *Aug. 10, 2010

(54) DIAGNOSTIC TEST DEVICE INCLUDING PHOTODETECTOR AND TETHER

(75) Inventors: Paul Duesbury, Cambridge (GB); Mark Davis, Beds (GB); Brett Cochrane, Northants (GB); Mark Burnapp, Beds (GB)

(73) Assignee: Church & Dwight Co., Inc., Princeton, NJ (US)

( * ) Notice: Subject to any disclaimer, the term of this patent is extended or adjusted under 35 U.S.C. 154(b) by 280 days.

This patent is subject to a terminal disclaimer.

(21) Appl. No.: 12/005,927

(22) Filed: Dec. 28, 2007

(65) Prior Publication Data

US 2008/0224719 A1    Sep. 18, 2008

(30) Foreign Application Priority Data

Dec. 29, 2006    (GB) ................................ 0626015.2

(51) Int. Cl.
*G01N 15/06*    (2006.01)
*G01N 21/49*    (2006.01)
*G01N 21/85*    (2006.01)

(52) U.S. Cl. ............... 250/573; 73/61.69; 422/82.05; 422/91; 436/169

(58) Field of Classification Search ................ 250/573; 422/56, 58, 61, 82.05, 91; 73/61.69, 61.48; 436/164, 169, 518, 805
See application file for complete search history.

(56) References Cited

U.S. PATENT DOCUMENTS

| 4,791,461 | A |   | 12/1988 | Kishimoto et al. | 356/446 |
| 6,555,060 | B1 |   | 4/2003 | Mauchan et al. | 422/52 |
| 6,821,531 | B2 |   | 11/2004 | Kumar | 424/488 |
| 6,960,170 | B2 |   | 11/2005 | Kuo | 600/551 |
| 7,622,729 | B2 | * | 11/2009 | Duesbury | 250/573 |
| 2002/0144747 | A1 | * | 10/2002 | Devlin, Sr. | 141/129 |
| 2002/0192833 | A1 | * | 12/2002 | Pan et al. | 436/164 |
| 2008/0253931 | A1 | * | 10/2008 | Duesbury et al. | 422/82.05 |

FOREIGN PATENT DOCUMENTS

EP    1564546 A1    8/2005

\* cited by examiner

*Primary Examiner*—Georgia Y Epps
*Assistant Examiner*—Francis M Legasse, Jr.
(74) *Attorney, Agent, or Firm*—Stuart D. Frenkel; Stephen B. Shear

(57) ABSTRACT

A diagnostic test device comprising means for sampling a liquid biological sample, means for reacting the sample with at least one reagent to provide one or more visible indicia and an optical detector for detecting the presence of said one or more indicia, the device further comprising a releasable tether which is released by contact with the liquid sample, thereby to cause the optical detector to detect the said one or more indicia.

18 Claims, 3 Drawing Sheets

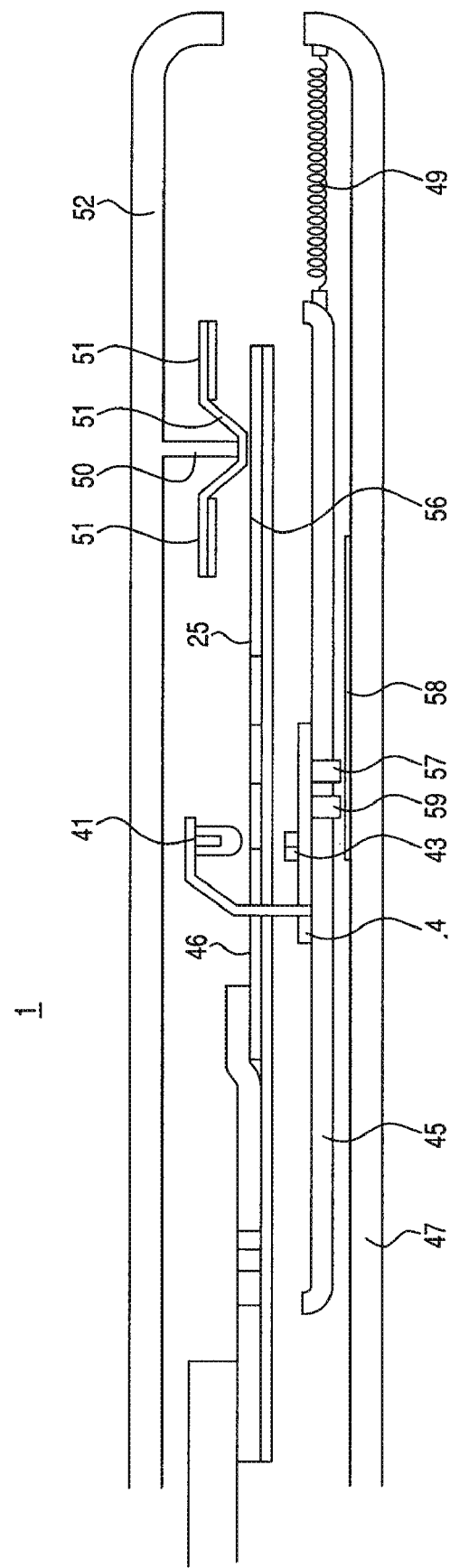

DIAGNOSTIC TEST DEVICE INCLUDING PHOTODETECTOR AND TETHER

FIELD OF THE INVENTION

The present invention relates to a diagnostic test device such as a pregnancy test device or a device such as for detection of a disease state, from a liquid biological sample. It may, for example, find application as a point of care (POC) diagnostic tool or other test device or for over-the-counter (OTC) sale. In such contexts, it is preferably a disposable device.

BACKGROUND OF THE INVENTION

It is now commonplace to provide a disposable diagnostic device for the analysis of a single analyte or multiple analytes that originate from a liquid biological sample. Examples of such devices include pregnancy tests and glucose meters for diabetics. In the case of a typical pregnancy test, urine is applied to a wick or collection zone, upon which the sample interacts and mixes with an antibody, or antibodies that specifically recognise the analyte of interest. One of the aforementioned antibodies is always coupled to a colourmetric indicator (often a gold sol or latex particle) for the visual interpretation of a result and often considered as the primary antibody.

The sample and the released components pass through the associated materials (often nitrocellulose) in a lateral flow manner. Deposited on to the nitrocellulose are two zones (or lines) of capture molecules. The first zone (or line) is often the second antibody of a pair that detects the presence of the analyte of interest, however in some embodiments this line is composed of avidin or streptavidin that binds to a biotin coupled to antibody. The second line is often deemed as a control line, and comprises an antibody that specifically recognises the primary antibody or a component bound to the surface of the colourmetric indicator.

The intensity of the first line of the two mentioned above is proportional to the quantity of analyte of interest present in the biological sample. This is deemed as the test line. The second line is used to confirm whether the test has operated correctly, by releasing the reagents, and fluid migrating appropriately. Together the lines represent the manner through which data can be extracted from the immobilised immunoassay that takes place within the device.

In purely visual (i.e. human eye dependent) test devices, a non-skilled user can be confused when a positive result is weak, it could be missed by the user, and considered as a negative, or provide the user with an ambiguous result leading to uncertainty. This may lead to inappropriate conclusions.

It would therefore be desirable to provide an automated, preferably electronic, detector system whereby the risk of inaccuracy can be reduced in terms of determining more reliably, whether there is sufficient contrast (colour change) between a test or control line zone and background and also, to ensure that the line intensities are read/interpreted at the appropriate time post sample application.

Furthermore, our unpublished co-pending application GB0603665.1 discloses the detection of active protease enzyme using a modified lateral flow immunoassay.

U.S. Pat. No. 4,791,461 discloses a portable analysis device comprising a housing and an optical system consisting of a light source and a photodetector. One or more test elements are mounted on a support strip and are used to perform an assay on a sample. The support is then placed in the housing and is caused to move relative to the housing and the optical system so that the photodetector produces a change in output signal indicative of the reaction of at least one of the test elements in response to the presence of a predetermined analyte in the sample.

SUMMARY OF THE INVENTION

Thus, the present invention provides a diagnostic test device comprising means for sampling a liquid biological sample, means for reacting the sample with at least one reagent to provide one or more visible indicia and an optical detector for detecting the presence of said one or more indicia, the device further comprising a releasable tether which is released by contact with the liquid sample, thereby to cause the optical detector to detect the said one or more indicia.

The releasable tether is preferably formed of a material which disintegrates when wet, eg a water-soluble or water-friable material.

Preferably, the complete device, including electronic circuitry, is formed integrally in a unitary device. Alternatively, it may be embodied as a device which does not include the circuitry for processing the photodetector output and that circuitry may then be housed in a separate unit into which the device is plugged to obtain a readout.

BRIEF DESCRIPTION OF THE DRAWINGS

FIG. 3 shows a variant of the construction shown in FIG. 2, representing an alternative embodiment of the invention.

DETAILED DESCRIPTION OF THE INVENTION

Figure 1:
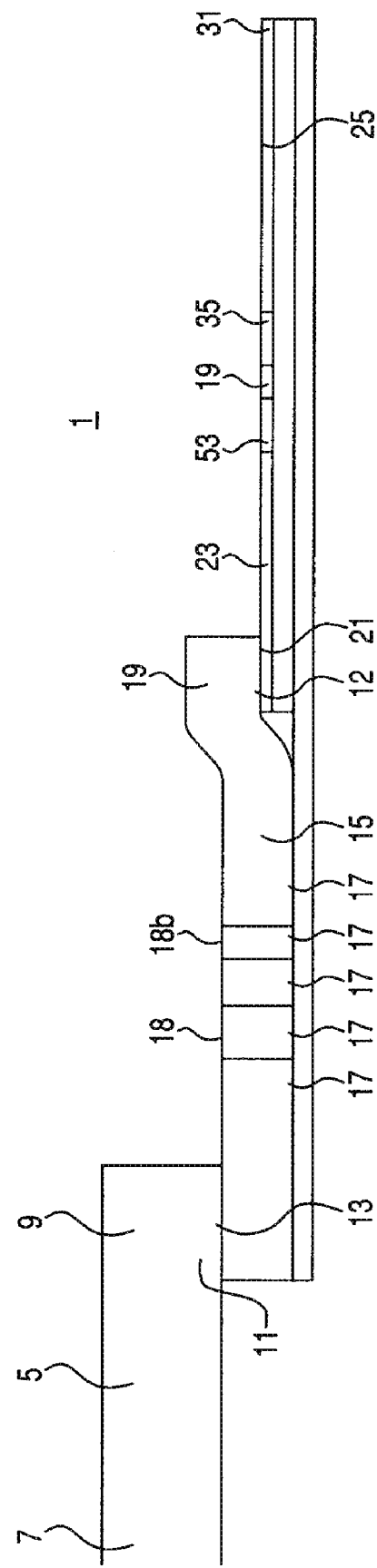
FIG. 1 shows an axial cross-section through part of a diagnostic test device according to the present invention.

In one preferred class of embodiments, the device according to the present invention preferably comprises a housing, preferably an elongate housing. The housing is not necessarily substantially closed but may be open at one or more positions thereon, for example at least to expose the sampling means. The housing is preferably substantially elongate. Typically, the overall length of such an elongate device is from 10 cm to 20 cm, preferably from 14 cm to 18 cm. Preferably, it has a width of from 1 cm to 3 cm, more preferably from 1.5 cm to 2 cm.

Detection of one or more indicia includes the situations where only the presence or absence of an indicium is determined (although this includes the situation where the intensity of a corresponding photodetector output is compared with a threshold), as well as quantitative or semi-quantitative determination of the intensity of an indicium.

In the preferred class of embodiments, it is also preferred to provide capillary flow means, a region of which constitutes all or part of the sampling means. Preferably also, the detection zone is provided by another region of the capillary flow means, most preferably the detection zone being spatially separated from the sampling means.

It is especially preferred that the capillary flow means is substantially elongate, the sampling means comprising a sampling zone at one end thereof, the sampling zone being separated from the detection zone by a reagent zone. In such embodiments a mobilised reagent may be present in the reagent zone such as a labelled antibody capable of binding to an analyte of interest. A region (eg formed as a line) capable of capturing reagent and/or analyte after their interaction may be present in the detection zone. When a labelled antibody is present in the reagent zone, the capture region in the detection zone may comprise a second antibody capable of binding to a different epitope of the analyte.

Where any one or more of the sampling zone, reagent zone and detection zone are zones of the capillary flow means, they may be formed of the same, or a different material, provided that the material or material(s) is or are chosen such as to permit flow from the sample zone to the detection zone, eg. by virtue of having progressively decreasing pore size or fibre size. Suitable such materials include nitrocellulose, polyvinylidene fluoride, blotting paper, glass fibre and compressed or non-compressed synthetic fabric fibres such as viscose or polyester, entangled fibres such as any of the foregoing or nylon membrane.

In a preferred class of embodiments, the one or more indica are located in a predetermined detection region. In such embodiments the optical detector preferably comprises a light source and a photodetector. The light source and photodetector may be arranged for detecting light reflected from the detection region. Alternatively, the source and detector may be arranged to determine transmissivity through a substrate which comprises the detection region.

The releasable tether is preferably arranged such that upon its release, relative movement occurs between the photodetector and/or the light source, and the detection region. Such movement may for example, be linear or rotational, for example a rotational movement of the light source and/or photodetector. Preferably at least part of the photodetector moves relative to the detection region and most preferably, relative to any housing. However, the alternative arrangement whereby the detection region e.g. of a sample strip, moves relative to the photodetector parts, for example as described in U.S. Pat. No. 4,791,461, is also possible.

The detector may comprise a light source and a photodetector arranged for detecting light reflected from the detection region. Alternatively, the source and detector may be arranged to determine transmissivity through the detection region.

A secondary movement detector may also be provided, e.g. also as a light source/photodetector arrangement to trigger, by means of a mark provided for the specific purpose of generating an output just before or just after detection of at least one of the indicia, is to be expected.

Also in a generally preferred arrangement, upon release, the photodetector and/or light source may be moved relative to the detection region by stored energy release means, such as spring means, for example a coil spring. Alternatively, the motive force, following release, may be provided by a miniature servomotor or other electrically operated device.

The releasable tether may comprise a material which disintegrates when wet, e.g. a water-soluble or water-friable material, such as a water soluble polymer (eg polyvinyl alcohol), gelatin, collagen, pectin, cellulose or sugar paper or any water-soluble organic or inorganic solid such as a sugar or an ionic salt such as an alkali metal chloride, hydroxypropylcellulose or hydroxymethyl cellulose, any of these optionally being admixed with a solubilising agent such as polyol, eg. glycerol.

Another alternative is to provide a material which disintegrates when wet, for example tissue paper, crepe paper, or cigarette paper or ethylene-acrylic acid sodium ionomers or microfibrillated cellulose, such as described in U.S. Pat. No. 6,821,531.

In yet another arrangement, the releasable tether may comprise fuse means which is arranged to burn-out or be melted by passage of an electrical current which is initiated substantially immediately by detection of moisture, or after a predetermined time period for example triggered by a conductivity sensor. An example of a 'melting fuse' is a wax member which is melted due to being heated by passage of the electrical current through a filament. When a conductivity sensor is employed, optionally, a suitable electrolyte may be impregnated into an appropriate substrate to allow passage of sufficient current through the conductivity sensor when wet.

The part or parts of the optical detector which move over the detection region is or are preferably mounted on a carriage, eg a carriage arranged to travel by virtue of a transport arrangement. For example, the carriage may comprise a projection arranged to travel in a slot or a slider disposed to move along a rail. Preferably, the transport arrangement comprises viscous damping means such as a predetermined amount of a viscous liquid disposed over the projection or slider. The viscous damping means slows and makes more uniform, the movement of the carriage so as to prevent unwanted effects such as vibration, which may interfere with the reading or abrupt termination of movement through the impact with a static object which is also capable of interference.

The detection region may also be provided with a stop indicator such as a black region or line. This is preferably situated near the end of the travel of the moving part(s) of the detector means. Its function is to provide a definite indication that a scan has occurred in the event that neither a visible measurement indication nor a visible control indication is produced.

The output of the optical detector is preferably processed by suitable circuitry to produce a display for providing a visible indication of the result of the test. This result may be qualitative (eg. the presence or absence of the analyte of choice) or it may be semi-quantitative (eg. an approximate value of analyte concentration in the sample).

Preferably, the device further comprises means for producing an electrical signal indicative of loading of the sample. Preferably also, the device includes electronic timer means for determining the time elapsed between production of the electrical signal indicative of loading of the sample and production of the photodetector pulsed output. Electronic means may be provided for determining whether the determined time is within a predetermined time range and thereby producing an output indicative of whether or not a diagnostic test is valid. In this kind of system, preferably the means for producing an electrical signal indicative of sample loading comprises a conductivity sensor.

An optional feature of the device is to provide the device with a wetness sensor which may form part of the releasable tether. However, a wetness sensor, preferably of the conductivity kind, eg using printed electrodes on any capillary flow means, may be used to activate the signal processing circuit. An appropriate circuit may be configured to be activated after a predetermined time delay from first sensing of moisture by the wetness detector. This helps to avoid generation of a false positive resulting from detection of a moving sample front in a capillary flow arrangement. For this purpose, the wetness detector may for example be positioned in a sampling zone, a reagent zone or in a detection zone, in the latter case preferably in a position which the sample front reaches before it reaches the position of the one or more indica.

The non-functional components of the device (e.g. other than optical detector, sampling means, any means for sample transfer, the detection region, and any circuitry or display) may be made from any one or more suitable materials but are preferably made from a mouldable plastics material such as ABS (Acrylonitrile-butadiene-styrene), acetals or polyoxymethylenes (POM, Delrins), acrylics, butyls or polyisobutylenes (polybutenes), ethylene copolymers [(poly)ethylene acrylate acid (EAA), (poly)ethylene methyl acrylate (EMAC), (poly)ethylene ethyl acrylate (EEA), (poly)ethylene vinyl acetate (EVA), (poly)ethylene butyl acrylate (EBAC), (poly)ethylene vinyl acetate (EVA or EVAC), (poly)ethylene vinyl alcohol (EVAL or EVOH), (poly)ethylene propyleneterpolymer (EPM)], fluoropolymers such as polytetrafluoroethylenes (PTFE) or polyvinylidene fluorides (PVDF), ionomers, liquid crystal polymers (LCP), PEEK or ketones (polyaryletherketones or polyetheretherketones), polyethylenes, polyamides (nylons), polycarbonates, thermoplastic polyesters or terphthalates (PET, PBT), polyethylenes, polyether block amides (PEBA), polyetherimides, polyimides, polyolefins, polyphenylene oxides (PPO), polyphenylene sulfides (PPS), polypropylenes (PP), polysulphones, polyphthalamides (Aramids), thermoplastic polyurethanes, polyvinylidene chloride (PVDC), styrene or polystyrene, styrene acrylonitrile copolymers (SAN, ASA, AES), styrene butadiene rubber (SBR), styrene maleic anhydride (SMA), vinyl or polyvinyl chlorides (PVC), polylactides (PLA) and ethylene-vinyl acetates. It is especially preferred if any housing, carriage and transport mechanisms are formed from a mouldable plastics material.

The optical detector is intended to produce an electrical output indicative of the result of the test, derived from detection of said one or more indica. As described further below, this may be processed by suitable circuitry and may be used to indicate the test result on a display.

The releasable tether is positioned such that it can be wetted by the sample when the sample reaches a predetermined position. Thus, where the device comprises capillary flow means, the releasable tether is preferably touching, or more preferably anchored to the capillary flow means. In any event, before release it must be attached so as to keep the movable part(s) of the photodetector, eg. by attachment to a carriage therefor, fixed relative to the body of the device.

Although a particularly preferred embodiment described below is in the form of a pregnancy test device, the present invention may also be realised in the form other diagnostic or similar test devices. The invention can be applied in any format that utilises multiple lines, areas of high/low contrast. Any assay format that has a line intensity change in relation to background, be it colour or fluorescence may employ the present invention, but it is optimal in context of an immunoassay, and lateral flow strip technology.

The present invention will now be explained in more detail by way of the following description of a preferred embodiment and with reference to the accompanying drawings.

FIG. 1 shows a first embodiment of a diagnostic test device 1 according to the present invention. It comprises an elongate structure 3 of generally planar configuration with its elongate dimension being shown from left to right in the drawing and its width being into the plane of the paper.

The device 1 comprises a sample collection wick 5 having a first sample collecting end 7 at one end of the wick 5. At the other end 9 of the wick, a lower surface 11 of the wick is in contact with an upper surface 13 of a reagent containing absorbent member 15, impregnated with two reagents shown in zone 17. This zone comprises, as visual reporter molecules or particles, gold sol particles conjugated to one of a binding pair of primary antibodies 18, and a second reagent containing the second of the antibody binding pair conjugated with biotin 18b. At the other end of the reagent containing absorbent member 15, its lower surface 12 in a region 19 is in physical contact with an upper surface 21 of one end 23 of an assay reaction area absorbent member 25.

The assay reaction area absorbent member 25 is impregnated with two linear zones 33 and 35 which respectively contain two reagents to constitute a test line 33 and a control line 35. The test line 33 contains avidin or streptavidin which specifically binds to the secondary antibody reagent 18b, and the control line 35 contains an anti-species antibody capable of specifically binding the primary antibody: gold conjugate 18 independently of sample antigen.

The device, the main components of which are shown in FIG. 1, also comprises a transmissive optical detector for detecting the presence or absence of colouration in the measurement line zone 33 and the control line zone 35, although this mechanism is not depicted in FIG. 1. The purpose is to detect establishment of a relevant coloured reaction product within a range of predetermined times after the time in which a liquid sample is applied to the distal end 7 of the sample wick 5.

Figure 2:
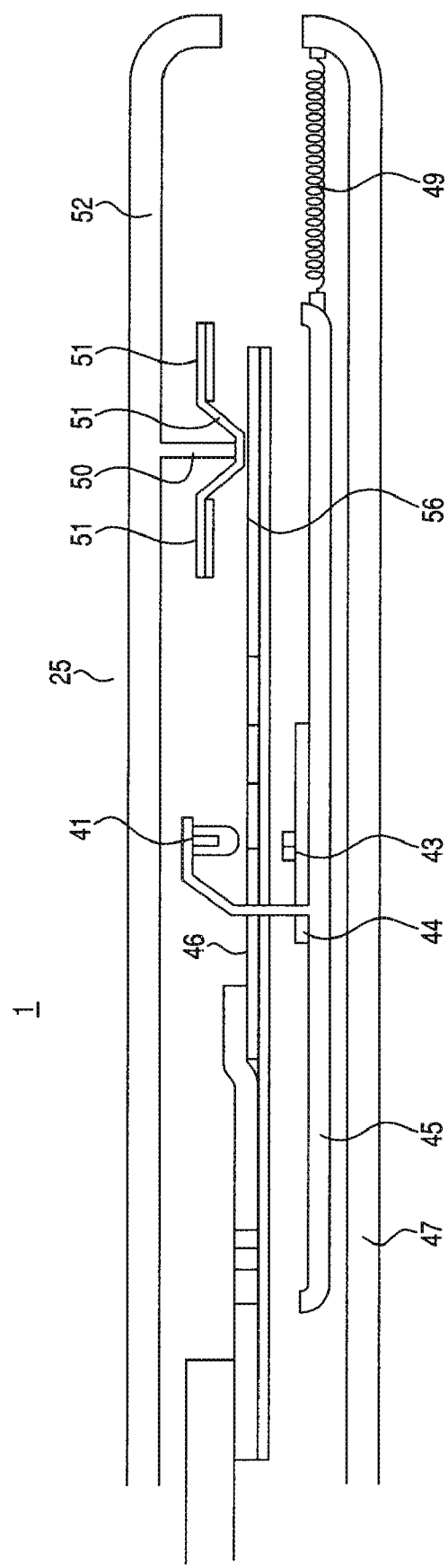
FIG. 2 shows an axial cross-section through the rear part of the device shown in FIG. 1, but depicting the optical detector system.

FIG. 2 shows in more detail the end of the device in the proximity of the distal end of the assay reaction area 31. This detector comprises an LED 41 and a phototransistor 43 mounted respectively above and below the plane of the assay reaction area absorbent member 25, and supported on a moveable carriage 45 which is in turn supported by a feature in the lower casework of the device 47. The carriage 45 and PCB 44, including the LED 41 and phototransistor 43 are held under tension by a coil spring 49 and a soluble tether 51 extending between the carriage 45 at location not on diagram, and an anchor point on the lower casework 47 of the device, also not shown on diagram. The soluble tether holds the optical arrangement 41 and 43 to the side of the assay reaction area to the proximal end 46 of the absorbent member.

Upon contact with sample, the soluble tether breaks at the point where a feature 50 in the upper casework 52 contacts the soluble tether 51 and distal end of absorbent member 56 releasing the energy retained within the pre-tensioned coil spring 49 and allowing the carriage 45 and associated components 41, 43, and 44 to traverse the assay reaction area coming to rest at the distal end of the absorbent member 56.

As it travels, the LED 41 passes over, and the phototransistor 43 travels directly beneath, the assay reaction area 33 and 35 in the absorbent member 25. The electronic output signal of the phototransistor 43 is conveyed via PCB 44 to circuitry integral with the device (not shown) to determine the relative contrast (optical density) between the two reaction zones 33 and 35 and background colour of the absorbent member 25. In this way, the presence or absence of either or both test lines in zones 33 and 35 is readily determined to produce an output indicative of (or not) of a clinical state of interest, such as pregnancy, and also the success or failure of the diagnostic test as a whole.

An alternative device for obtaining a semi-quantitative protease assay is constructed in similar manner to the device of FIGS. 1 and 2, except the numerals used to depict certain features represent different features in the protease assay device. In one embodiment an extra reagent of a purified protein, in this case human chorionic gonadotrophin (hCG) is provided in an external vessel to which the protease sample is added and given sufficient time to react with the purified protein. Following incubation the sample is added to the device and allowed to migrate along the test strip and into the absorbent member where the protein or its digested fragments are captured by the test line one 33.

If the sample contains no protease the hCG remains intact and signal generation is strong at test line one 33 or of a decreasing signal intensity with increasing concentrations of protease. In addition, the test line two 35 intensity (control line in a pregnancy test) is correspondingly opposed to that of the test line one, thus providing a second indication of protease activity (e.g. test line 1 strong, test line 2 weak in low protease sample, test line 1 weak and test line 2 strong in high protease activity).

In a second embodiment the reagent containing absorbent member 15 may contain an extra reagent of the purified protein, in this case human chorionic gonadotrophin (hCG). Interposed between the lower surface 12 of the reagent containing absorbent member 15, in a region 19 and the upper surface 21 of one end 23 of an assay reaction area of absorbent member 25 can be a soluble film that temporarily retards the flow of sample through the liquid path of the device. Importantly, the delay occurs once the sample (containing the protease of interest) has interacted with the labelled components and released the visual reporter molecules. This pause in flow enables the proteolytic enzymes to act on the protease-sensitive peptides without the need of an additional incubation step or complicated mechanical intervention. When the soluble film has dissolved the test runs according to description above.

The said soluble film can be composed of, but not limited to; PVA, pectin, cellulose, modified cellulose, gelatine etc.

In general, the number of lines (indicia) located within the assay reaction area absorbent member 25 may optionally be greater than 2. For example, two or more first lines may be provided, each having labelled components with protease-sensitive linker peptides which are sensitive to different proteases. In such embodiments where each of the first lines has a different label, a plurality of second lines may be provided each capable of binding only one of the different labels. In this way, the presence of multiple different proteases may be detected in the sample.

In an alternative embodiment of the semi-quantitative protease assay device, the structure shown in FIG. 2 may optionally be modified by the inclusion of a movement detector, although this is not absolutely necessary. This variant is shown in FIG. 3. A second photodetector 57 is employed to record the contrast between a line and background bar code arrangement 58 within the device housing. This arrangement utilises a specific illuminating LED 59. Alternatively, the existing illumination LED 41 may be adopted for that purpose. However, in this alternative embodiment, the PCB 44 generates a signal which is indicative of the relative intensity of the first and second lines and thus the relative activity of the protease enzyme in the sample.

In the light of the described embodiment, modifications of that embodiment, as well as other embodiments, all within the scope of the present invention as defined by the appended claims will now become apparent to persons skilled in the art.

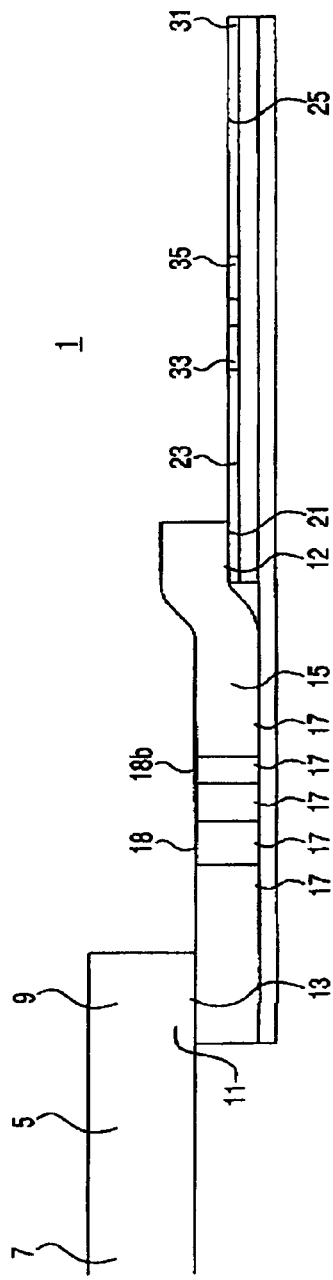

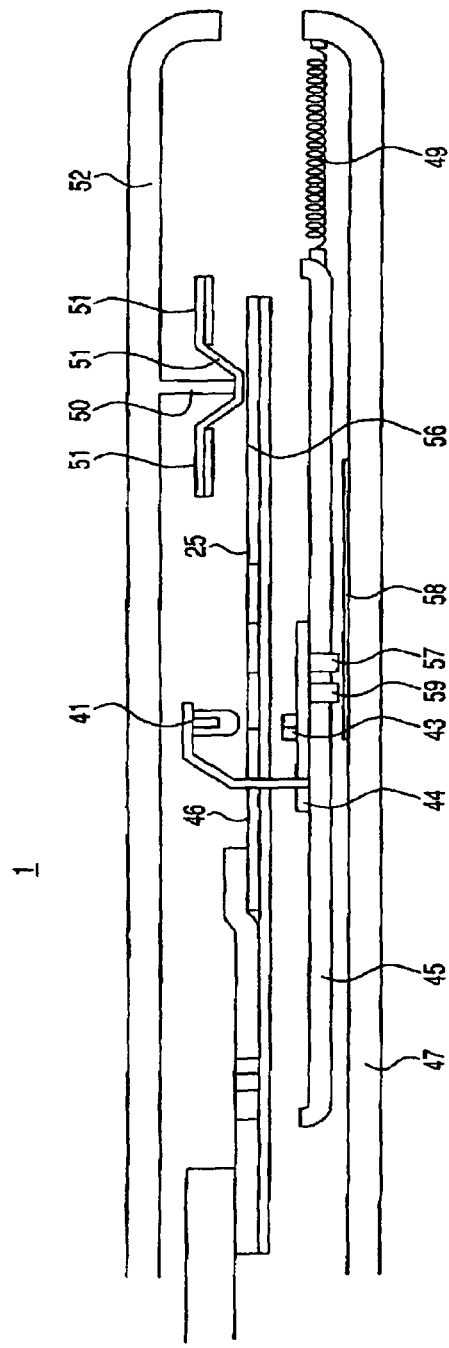

The invention claimed is:

1. A diagnostic test device comprising means for sampling a liquid biological sample, means for reacting the sample with at least one reagent to provide one or more visible indicia and an optical detector for detecting the presence of said one or more indicia, the device further comprising a releasable tether which is released by contact with the liquid sample, thereby to cause the optical detector to detect the said one or more indicia.

2. A device according to claim 1, wherein the optical detector comprises a light source and a photodetector, the said one or more indicia being located in a predetermined detection region.

3. A device according to claim 2, wherein the optical detector comprises a light source and a photodetector arranged for detecting light reflected from the detection region.

4. A device according to claim 2, wherein the optical detector comprises a light source and a photodetector arranged for detecting light transmitted through the detection region.

5. A device according to claim 2, wherein the releasable tether is arranged such that upon its release, relative movement occurs between the photodetector and/or the light source and the detection region.

6. A device according to claim 5, wherein the relative movement is completed within a time period of from 0.1 to 2 seconds.

7. A device according to claim 5, wherein said relative movement is linear movement.

8. A device according to claim 5, wherein said relative movement is rotary.

9. A device according to claim 5, further comprising damping means for damping said movement.

10. A device according to claim 8, wherein said rotary relative movement is rotational movement of the light source and/or photodetector.

11. A device according to claim 5, wherein upon release, the photodetector and/or light source is or are moved relative to the detection region by spring means.

12. A device according to claim 5, wherein upon release, the photodetector and/or light source is or are arranged to be moved by one or more of gravity, inertia, gas release and electromotive means.

13. A device according to claim 5, wherein the releasable tether comprises a water-soluble material.

14. A device according to claim 13, wherein the water-soluble material is selected from a water-soluble polymer such as polyvinyl alcohol, collagen, gelatin, pectin or sugar paper or any water-soluble organic or inorganic sold such as a sugar or an ionic salt such as an alkali metal chloride, hydroxymethyl cellulose or hydroxypropyl cellulose, any of said materials optionally being in admixture with a solubilising agent such as a polyol, eg glycerol.

15. A device according to claim 5, wherein the releasable tether comprises a material which disintegrates when wet.

16. A device according to claim 15, wherein the material which disintegrates when wet is selected from tissue paper, crepe paper, or cigarette paper or ethylene-acrylic acid sodium ionomers or microfibrillated cellulose.

17. A device according to claim 5, wherein the releasable tether comprises fuse means which is burned-out or melted by virtue of passage of an electrical current which is initiated by detection of moisture.

18. A device according to claim 17, further comprising a conductivity sensor for detection of the moisture.

\* \* \* \* \*

UNITED STATES PATENT AND TRADEMARK OFFICE
CERTIFICATE OF CORRECTION

| | | |
|---|---|---|
| PATENT NO. | : 7,772,578 B2 | |
| APPLICATION NO. | : 12/005927 | |
| DATED | : August 10, 2010 | |
| INVENTOR(S) | : Duesbury et al. | |

It is certified that error appears in the above-identified patent and that said Letters Patent is hereby corrected as shown below:

In the drawing sheets, consisting of Figs. 1 and 3, should be deleted to be replaced with the drawing sheets, consisting of Figs. 1 and 3, as shown on the attached pages.

Signed and Sealed this
Twenty-sixth Day of April, 2011

David J. Kappos
*Director of the United States Patent and Trademark Office*